US012268402B2

(12) United States Patent
Biedermann et al.

(10) Patent No.: US 12,268,402 B2
(45) Date of Patent: Apr. 8, 2025

(54) SURGICAL INSTRUMENT

(71) Applicant: BIEDERMANN TECHNOLOGIES GMBH & CO. KG, Donaueschingen (DE)

(72) Inventors: Timo Biedermann, Trossingen (DE); Achim Schünemann, Villingen-Schwenningen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 17/224,741

(22) Filed: Apr. 7, 2021

(65) Prior Publication Data

US 2021/0315592 A1 Oct. 14, 2021

Related U.S. Application Data

(60) Provisional application No. 63/007,532, filed on Apr. 9, 2020.

(30) Foreign Application Priority Data

Apr. 9, 2020 (EP) .................................... 20169076

(51) Int. Cl.
*A61B 17/16* (2006.01)
*A61B 17/00* (2006.01)
*A61B 17/70* (2006.01)

(52) U.S. Cl.
CPC ...... *A61B 17/1697* (2013.01); *A61B 17/7077* (2013.01); *A61B 2017/00367* (2013.01); *A61B 2017/0046* (2013.01)

(58) Field of Classification Search
CPC ............ A61B 17/1697; A61B 17/1753; A61B 17/7076; A61B 17/7082; A61B 17/8875
See application file for complete search history.

(56) References Cited

U.S. PATENT DOCUMENTS 4,262,676 A * 4/1981 Jamshidi ............ A61B 10/0283
600/566
5,522,398 A * 6/1996 Goldenberg ......... A61B 10/025
600/562

(Continued)

FOREIGN PATENT DOCUMENTS

EP 2 289 433 A2 3/2011
EP 3 524 181 A1 8/2019

OTHER PUBLICATIONS

European Search Report for Application No. 20 169 076.5, mailed Oct. 5, 2020, 3 pages.

*Primary Examiner* — Matthew J Lawson
(74) *Attorney, Agent, or Firm* — Womble Bond Dickinson (US) LLP

(57) ABSTRACT

A surgical instrument includes a handle having first and second ends and a passage that extends between the ends, wherein a maximum height of the handle is less than a lateral length of the handle, a shaft having first and second ends and a longitudinal axis that extends between the ends, and a coaxial channel that extends completely through the shaft, wherein the shaft is releasably connectable to the handle when the first end of the shaft is inserted from the second end of the handle into the passage to a position closer to the first end of the handle than to the second end of the handle, and a secondary instrument configured to be inserted from the first end of the shaft into the channel and to extend out of the second end of the shaft when the shaft and the handle are connected to one another.

20 Claims, 10 Drawing Sheets

(56) References Cited

U.S. PATENT DOCUMENTS

| | | | |
|---|---|---|---|
| 6,221,029 B1* | 4/2001 | Mathis | A61B 10/0233 |
| | | | 600/564 |
| 8,702,741 B2 | 4/2014 | Jäggi et al. | |
| 9,763,722 B2 | 9/2017 | Roybal | |
| 10,117,664 B2* | 11/2018 | Rudser | A61M 60/861 |
| 10,624,652 B2* | 4/2020 | Germain | A61B 17/1631 |
| 11,529,199 B2* | 12/2022 | Elliot | A61B 90/361 |
| 2008/0154279 A1 | 6/2008 | Schumacher et al. | |
| 2009/0076520 A1* | 3/2009 | Choi | A61B 17/3472 |
| | | | 606/108 |
| 2009/0275954 A1* | 11/2009 | Phan | A61B 17/8883 |
| | | | 606/53 |
| 2011/0054537 A1* | 3/2011 | Miller | A61B 17/1655 |
| | | | 606/279 |
| 2016/0030100 A1* | 2/2016 | Divincenzo | A61B 17/7091 |
| | | | 606/104 |
| 2016/0296266 A1 | 10/2016 | Chandanson et al. | |
| 2019/0209154 A1* | 7/2019 | Richter | A61B 1/00091 |
| 2019/0247102 A1 | 8/2019 | Biedermann | |

* cited by examiner

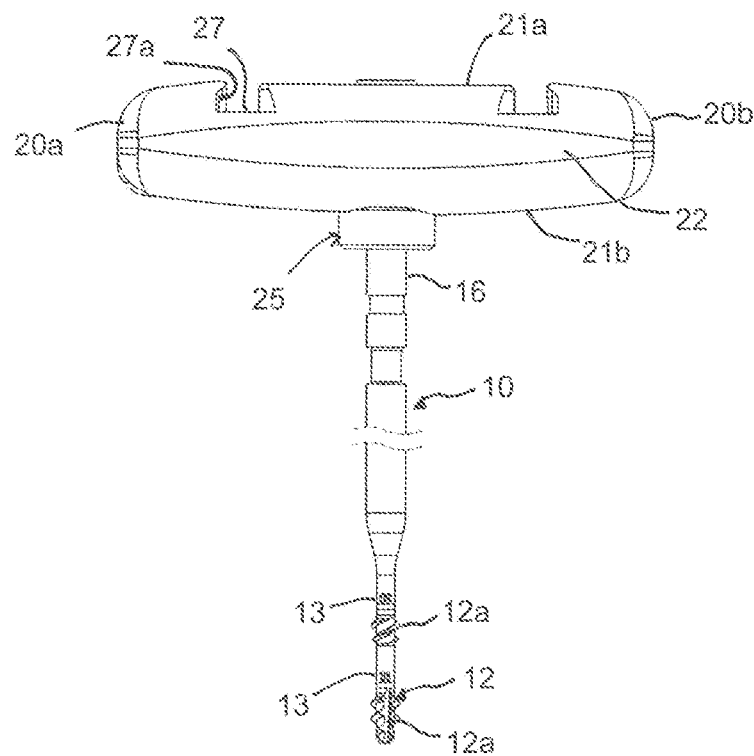
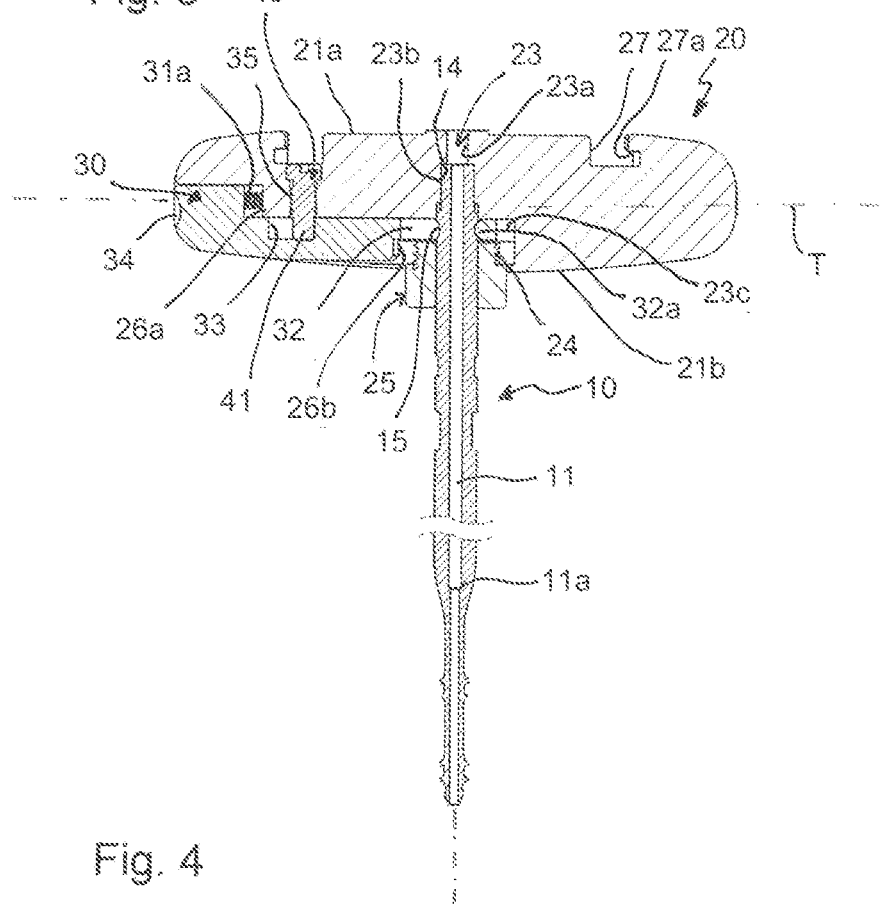
Fig. 3
Fig. 4

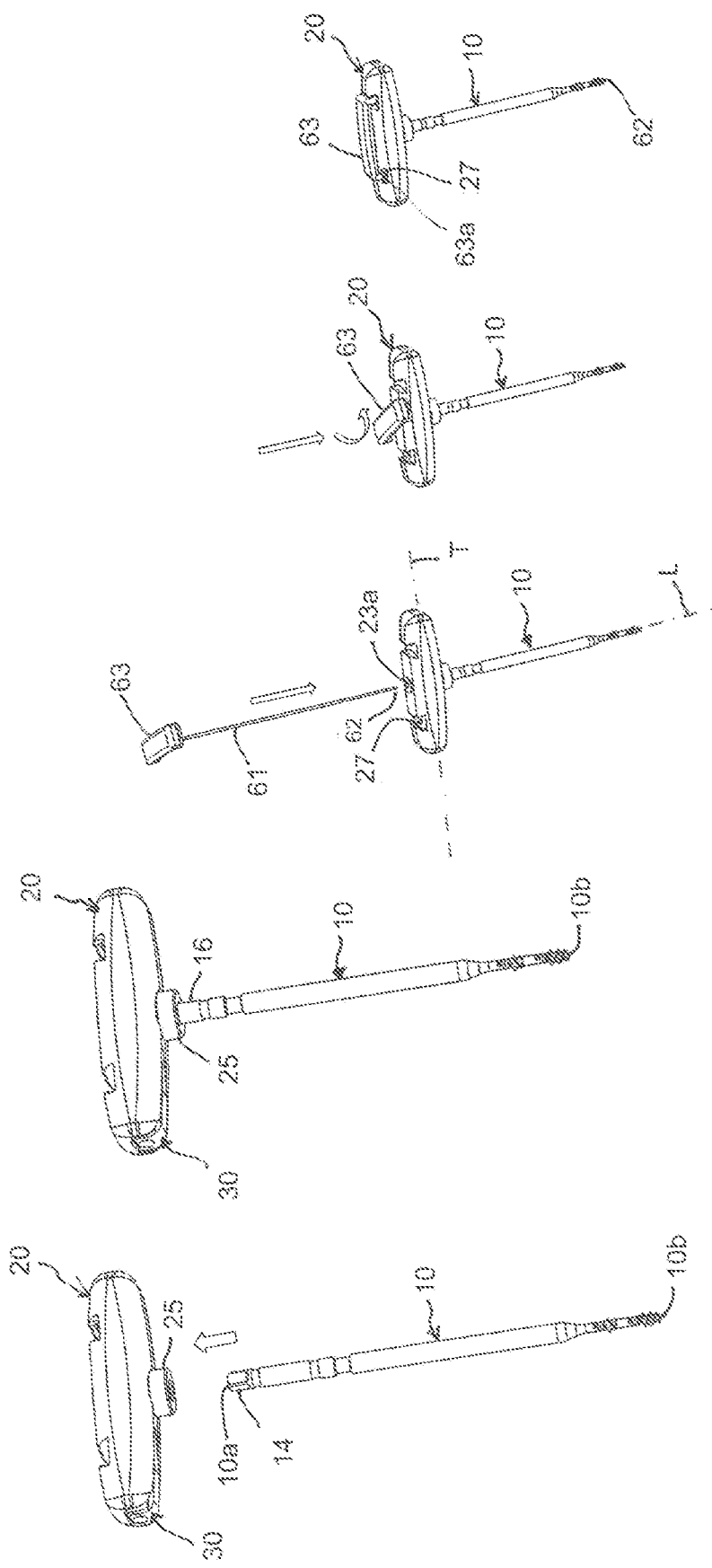

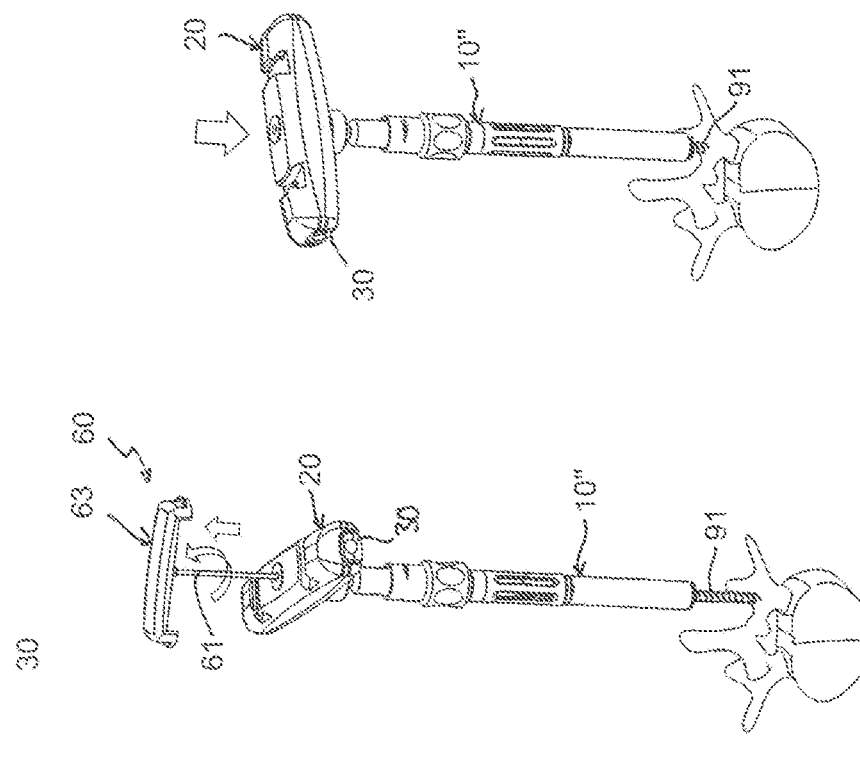
Fig. 14d
Fig. 14c
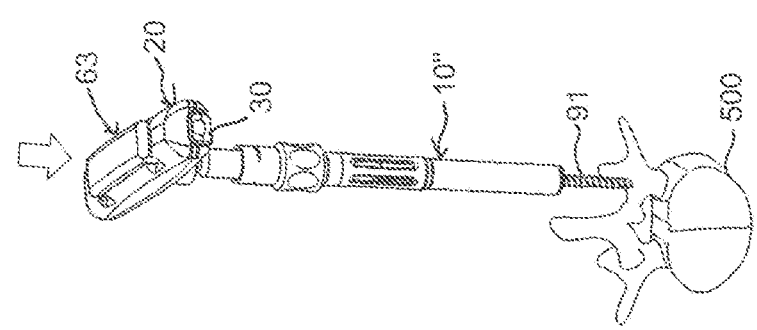
Fig. 14b
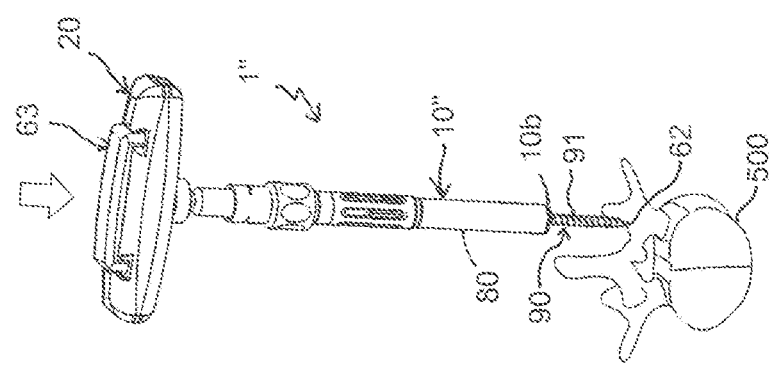
Fig. 14a

SURGICAL INSTRUMENT

CROSS-REFERENCE TO RELATED APPLICATION(S)

The present application claims priority to and the benefit of U.S. Provisional Patent Application No. 63/007,532, filed Apr. 9, 2020, the contents of which are hereby incorporated by reference in their entirety, and claims priority from European Patent Application EP 20 169 076.5, filed Apr. 9, 2020, the contents of which are hereby incorporated by reference in their entirety.

BACKGROUND

Field

The application relates to a surgical instrument including a handle portion and an exchangeable instrument shaft. The surgical instrument may be used in musculoskeletal surgery, and in particular, in spinal surgery.

Description of Related Art

In surgery of the spine, a known technique involves the use of Jamshidi needles for inserting Kirschner wires (K-wires), which may be used for the placement of bone anchors such as pedicle screws. According to the known method, first, a small incision is made in the skin of the patient. Then, a Jamshidi needle including a tiny awl is advanced through the incision to the bone. A bore is prepared by hammering and turning the Jamshidi needle back and forth, and then the awl is removed. Subsequently, a K-wire is placed into the hole and the Jamshidi needle is removed. A thread cutter is guided by the K-wire to the hole, and a thread is cut with the thread cutter. After cutting the thread, the thread cutter is screwed back. Finally, a cannulated bone screw is guided by the K-wire to and screwed into the threaded hole. As a last step, the K-wire is removed. In sum, these steps require the use of several instruments and several instrument passes, and may be time consuming, especially in cases where many threaded bores have to be prepared.

SUMMARY

It is an object of the invention to provide an improved surgical instrument, a kit including such a surgical instrument and at least one further exchangeable part, and a system including a surgical instrument or a kit and a bone anchor, which allows for the reduction of surgical steps and the carrying out of certain surgical steps more efficiently.

According to an embodiment, the surgical instrument includes a handle portion and an elongate cannulated instrument shaft which is releasably connectable to the handle portion. The instrument shaft may have a functional section at its free end which is configured to perform a function during surgery. With the instrument, it is possible to reduce the number of steps necessary for certain surgical methods, for example, for the placement of a pedicle screw into the pedicle of a vertebra. Therefore, the number of steps can be reduced and time can be saved during surgery.

The surgical instrument may further include a secondary instrument configured to be inserted and removed through the handle portion into the instrument shaft. Such a secondary instrument may be, for example, an elongate shaft with a tip such as an awl. This awl may have one of various tips such as a blunt, sharp, or threaded tip. Alternatively, the secondary instrument may be, for example, a K-wire, a depth measuring gauge, a sensor, or a syringe, or any other suitable instrument configured to pass through the instrument shaft.

The connection between the instrument shaft and the handle portion may be a standardized connection, such as, for example, a quarter inch female-male connection. This allows the use of various other instrument shafts with different functions in an interchangeable manner. The attachment and detachment of the instrument shaft to the handle portion can be carried out without using a further tool. Hence, the variety of applications of the surgical instrument can be considerably increased. Moreover, the surgical instrument has a simple structure and can be easily and quickly assembled.

In one embodiment, the surgical instrument may include an instrument shaft with an end portion formed as a thread cutter and with an awl as a secondary instrument to be inserted into the channel of the cannulated instrument shaft.

The surgical instrument may be used, in particular, together with a cannulated bone anchor.

An embodiment of a method of placing a bone anchor, such as a bone screw, may involve the following steps. After an incision has been made in the skin, a surgical instrument having an instrument shaft with a thread cutter and with an awl inserted into the instrument shaft is applied to the bone. Next, the cortical bone is opened and a thread is cut into the bone. Subsequently, the awl is removed and a K-wire is inserted through the channel of the instrument shaft. Thereafter, the instrument shaft is removed. Finally, the bone screw may be placed via the K-wire, and the K-wire can be removed. In an alternative embodiment of a method of placing a bone anchor, in particular, a pedicle screw, the instrument shaft includes a shank inserting device configured to fixedly hold a bone anchor, for example, a head of an anchoring element of a polyaxial bone anchor, so that the threaded shank can be directly screwed into bone. An awl inserted through the shank inserting device may be used for penetrating the cortical bone. This may involve awls of different types and lengths, as well as modular awls to allow for various length options or uses. In the alternative embodiment, use of a thread cutter is not necessary, which makes the method even more efficient. This approach also has the advantage where the awl can be removed before the screw is fully advanced, thereby reducing the risk of vascular or neurological injuries.

In a further development, an adapter member can be attached between the instrument shaft and the handle portion. Such an adapter member may include, for example, a navigation device for image based navigation of the surgical steps and robotic guidance.

BRIEF DESCRIPTION OF THE DRAWINGS

Further features and advantages of the invention will become apparent from the description of embodiments by means of the accompanying drawings. In the drawings:

FIG. 3 shows a side view of the instrument of FIGS. 1 and 2.

FIG. 4 shows a cross-sectional view of the instrument of FIGS. 1 to 3, with the cross-section taken in a plane extending through a longitudinal axis of a shaft of the instrument and through a handle portion of the instrument in a lengthwise direction.

FIGS. 10a to 10e show perspective views of steps of assembling the surgical instrument according to the embodiment of FIGS. 1 to 9.

FIGS. 14a to 14d show perspective views of steps for using a further embodiment of the surgical instrument to place a pedicle screw into the pedicle of a vertebra.

DETAILED DESCRIPTION

Figure 1:
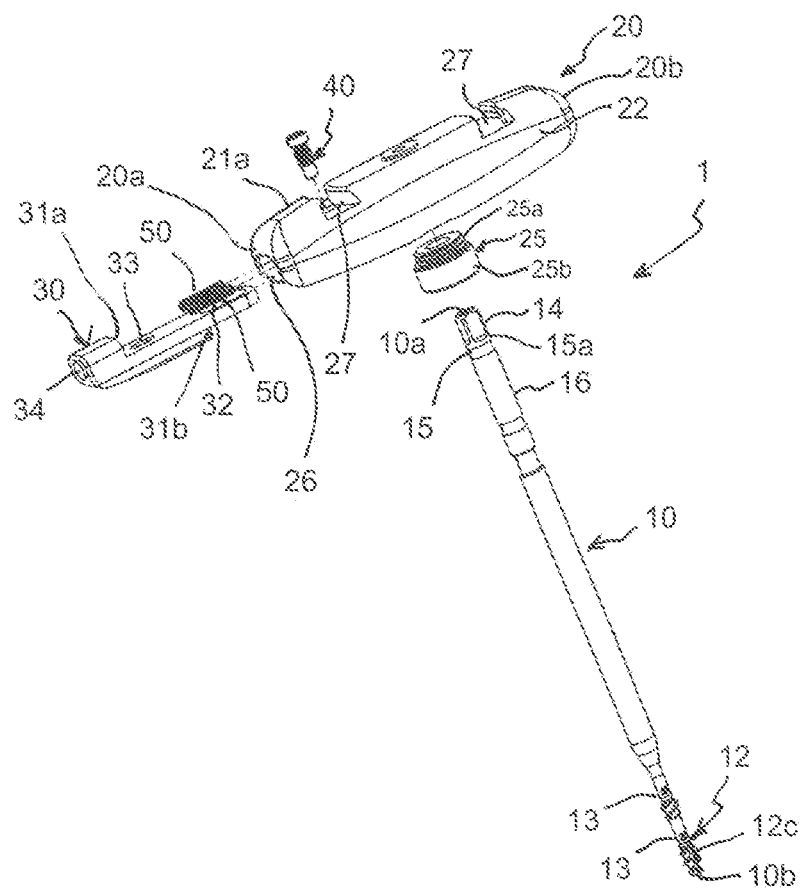
FIG. 1 shows an exploded perspective view of a surgical instrument according to an embodiment of the invention.
Figure 2:
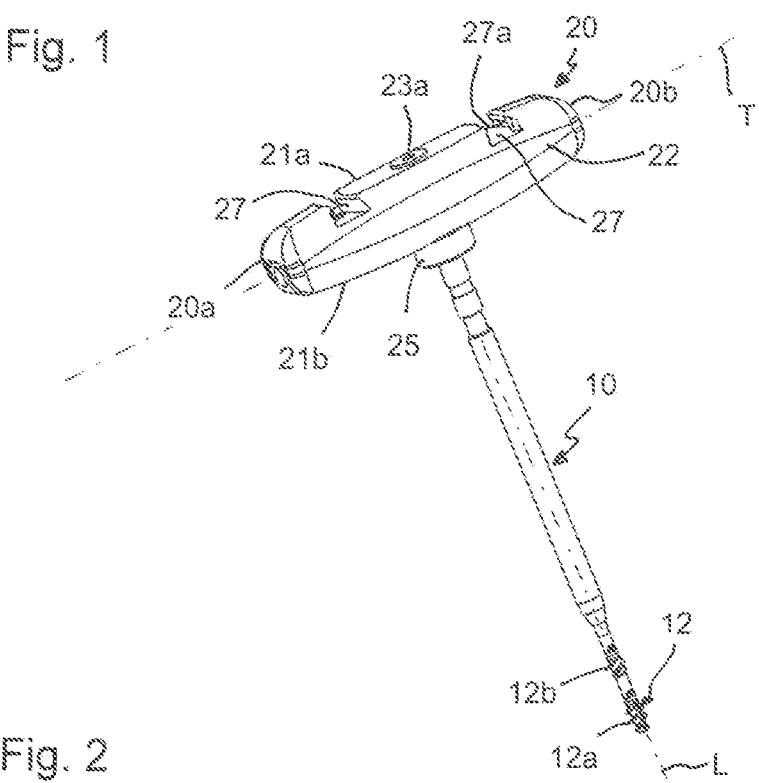
FIG. 2 shows a perspective view of the instrument of FIG. 1 in an assembled state.
Figures 5, 6:
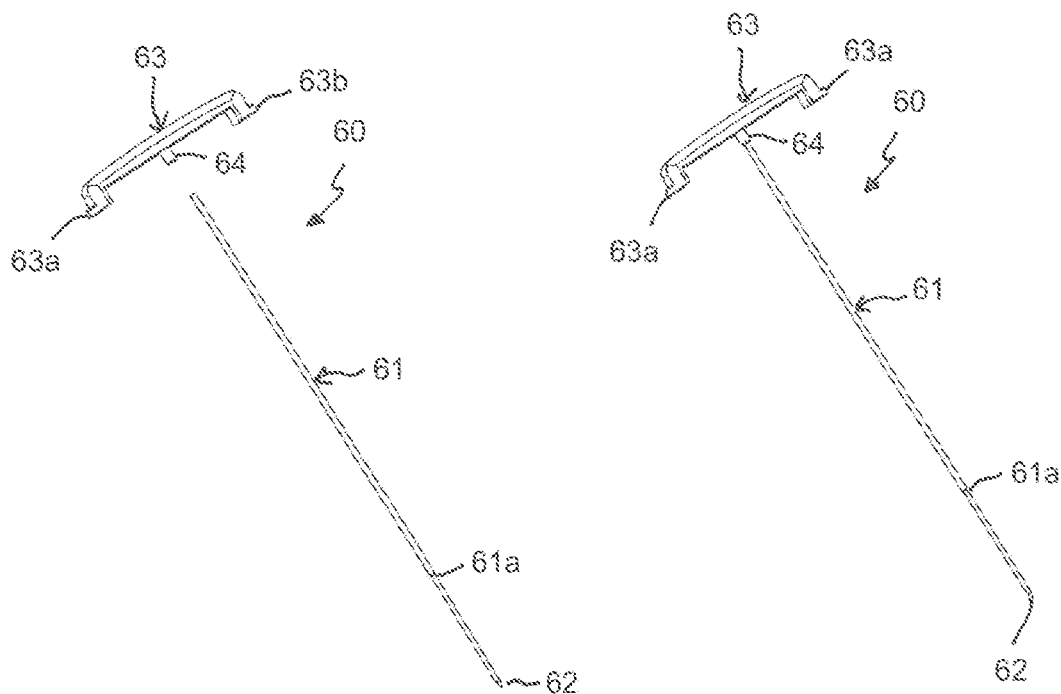
FIG. 5 shows an exploded perspective view of a secondary instrument in the form of an awl.
FIG. 6 shows a perspective view of the secondary instrument of FIG. 5 in an assembled state.
Figure 7:
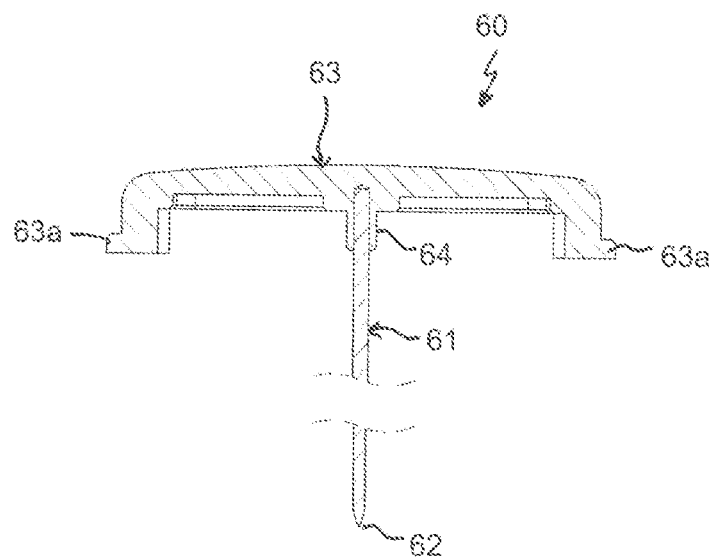
FIG. 7 shows a cross-sectional view of the secondary instrument of FIGS. 5 and 6, with the cross-section taken in a plane including a shaft axis of the secondary instrument and extending through elongate ends of an attachment portion of the secondary instrument.
Figure 8:
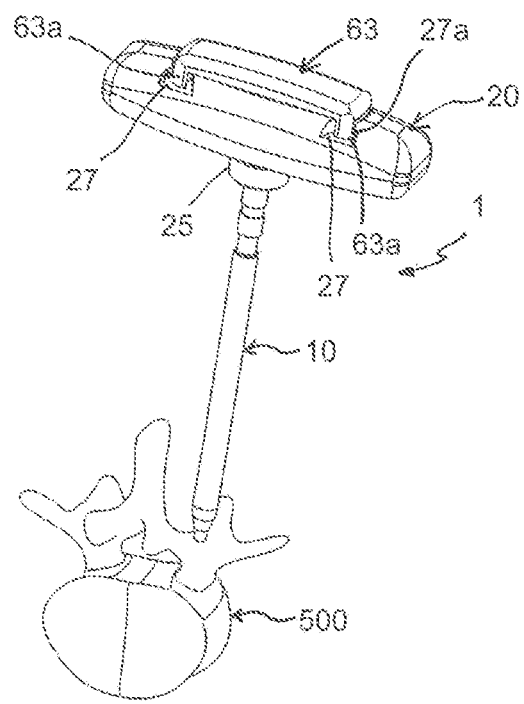
FIG. 8 shows a perspective view of use of the surgical instrument according to the embodiment of FIGS. 1 to 7 applied to a vertebra.

An embodiment of a surgical instrument 1 will be described with reference to FIGS. 1 to 4. The surgical instrument 1 includes an elongate instrument shaft 10 that is releasably connectable to a handle portion 20. The instrument shaft has a first or rear end 10a and an opposite second or front end 10b. A channel 11 extends completely through the instrument shaft from the rear end 10a to the front end 10b and defines a longitudinal axis L. The channel 11 is sized to receive a secondary instrument therein, for example, an awl as described below, or a K-wire, or a syringe, or any other suitable elongate member. The channel 11 may have a constant or a varying inner width. For example, a step 11a may be formed to reduce a width of the channel towards the front end 10b and to provide a stop that limits the insertion depth of the secondary instrument. Adjacent to the front end 10b, the instrument shaft includes a functional section 12 configured to perform an instrument function. In the embodiment, the functional section 12 is a thread cutter. The thread cutter may include a single thread cutting section, or may include more than one thread cutting sections 12a, 12b that may be arranged at smaller or greater distances from the front end 10b. In greater detail, a first thread cutting section 12a may be arranged at or close to the front end 10a and a second thread cutting section 12b may be arranged at a distance from the first thread cutting section 12a. The thread cutting sections are configured to cut a thread into bone. One or more longitudinal grooves 12c in the thread cutting section 12a may facilitate the cutting step. As shown in particular in FIG. 3, at the rear end of the one or more thread cutting sections, depth indication marks 13 may be provided that are configured to indicate the depth to which the thread cutting section is advanced into bone.

At the rear end 10a of the instrument shaft 10, a connection portion is formed that is configured to connect the instrument shaft 10 in a releasable manner to the handle portion 20. In the embodiment, the connection portion 14 may be designed as a male connection portion with a polygon outer contour, such as a square end. In a specific embodiment, the connection portion may be a quarter inch connection portion as used in many standard couplings. At a side of the connection portion 14 opposite to the rear end 10a, a circumferential groove 15 may be formed that is configured to be engaged by an engagement portion of a pushing member as described below to hold the instrument shaft 10 within the handle portion 20. The edge of the connection portion 14 towards the groove 15 forms a circumferentially extending protrusion or bulge 15a.

The outer contour of the instrument shaft 10 may have various shapes and is not limited to the detailed shape as depicted in the figures. Since in this embodiment, the functional section 12 is a thread cutting section, the longitudinal axis L is also an axis of rotation of the surgical instrument. It shall be noted, however, that other instrument shafts with different functional sections may be provided which do not involve rotation. Adjacent to the groove 15, there may be a section 16 with a substantially constant outer diameter that is configured to fit into a guiding sleeve provided at the handle portion. This may increase the stability of the connection between the handle portion and the instrument shaft. Lastly, the thread cutting sections 12 may have a reduced outer diameter compared to other portions of the instrument shaft.

The instrument shaft may be made of any material, preferably however, of titanium or stainless steel or of any bio-compatible metal or metal alloy or plastic material. For a bio-compatible alloy, a NiTi alloy, for example Nitinol, may be used. Bio-compatible plastic materials may be, for example, polyether ether ketone (PEEK) or poly-L-lactide acid (PLLA).

Turning now to the handle portion 20, the overall shape of the handle portion may be that of an elongate bar or substantially cuboid-shaped body with rounded edges and outwardly bulged long sides to facilitate gripping. The handle portion 20 has a first end surface 20a and an opposite second end surface 20b, a top surface 21a and a bottom surface 21b opposite to the top surface, and side surfaces 22 connecting the top and bottom surfaces. The extension in the lengthwise direction along the top, bottom and side surfaces may be greater than in the height or width directions. A longitudinal axis T extends through the center of the handle portion in the lengthwise direction. In the assembled state, the longitudinal axis T of the handle portion 20 is substantially perpendicular to the longitudinal axis L of the instrument shaft 10, so that the surgical instrument 1 has an overall T-shape.

As can be seen in greater detail in FIG. 4, a passage 23 is provided that extends from the top surface 21a to the bottom surface 21b and permits insertion of the instrument shaft 10 and a secondary instrument, such as an awl or a K-wire or any other device. The passage 23 is substantially coaxial to the longitudinal axis L of the instrument shaft. In greater detail, the passage 23 may have a first portion 23a that is configured to receive, and preferably guide, the secondary instrument. An inner diameter of the first portion 23a may be slightly greater than an inner diameter of the channel 11 of the instrument shaft. Adjacent to the first portion 23a, there may be a second portion 23b that has an inner contour adapted to the contour of the connection portion 14 of the instrument shaft, which in the embodiment shown is a quarter inch female socket contour to receive the connection portion 14. Thus, the second portion 23b forms a connection structure configured to connect the handle portion 20 to the instrument shaft 10. As the second portion 23b has a greater inner width than the first portion 23a of the passage 23, a step is formed therebetween which provides an abutment for the rear end 10a of the instrument shaft 10. Moreover, the second portion 23b may followed by a small widening passage to permit the circumferential bulge 15a of the instrument shaft 10 to extend at least partially therein.

At the bottom side 21b of the handle portion 20, a threaded bore 24 forms part of the passage 23. An inner diameter of the threaded bore 24 is greater than that of the connection portion 23b. The threaded bore 24 is configured to receive a guiding sleeve 25 therein. The guiding sleeve 25 has a threaded portion 25a and may have a cylindrical unthreaded portion 25b with a greater diameter than the threaded portion 25a, such that when the guiding sleeve 25 is screwed into the threaded bore 24, the unthreaded portion 25b forms a stop and projects away from the bottom surface 21b. An inner diameter of the guiding sleeve 25 is such that the instrument shaft 10 can pass therethrough and can slide therein, in particular with its cylindrical section 16. As depicted in FIG. 4, between the threaded bore 24 and the connection portion 23b, an unthreaded section 23c of the passage 23 serves for receiving a portion of a pushing member 30.

As depicted specifically in FIGS. 1 and 4, a recess or cutout 26 is formed in the handle portion 20 for receiving the pushing member 30. The cutout 26 extends from the first end surface 20a into the unthreaded section 23c of the passage 23 in the lengthwise direction, i.e., in the direction of the axis T. In the height direction, i.e., in a direction perpendicular to the axis T, the cutout 26 has a stepped shape. In the region of the first end surface 20a of the handle portion, the cutout 26 extends to about half or more of the height of the first end surface 20a. At a position away from the first end surface 20a, the height of the cutout 26 is reduced, so that a first abutment 26a perpendicular to the axis T is formed at a distance from the first end surface 20a. The first abutment 26a serves for receiving a biasing member in the form of, for example, springs 50 between the pushing member 30 and the abutment 26a. A second abutment 26b is formed close to the bottom surface 21b and to the threaded bore 24, which faces away from the threaded bore 24. The second abutment 26b forms a stop for the pushing member 30 when the pushing member 30 is pushed inward, i.e., in the direction of the second end surface 20b.

The pushing member 30 may have an overall shape such that the pushing member is substantially flush with the outer surface of the handle portion 20 when inserted into the cutout 26. Moreover, the pushing member has a stepped shape which is substantially adapted to the shape of the cutout 26. With this shape, a first abutment surface 31a is formed at the pushing member 30 which is configured to face the first abutment surface 26a of the handle portion 20, and a second abutment surface 31b which faces the second abutment surface 26b of the handle portion. The pushing member has a smallest height on a side of the free end that extends past the second abutment 31b, which is configured to extend into the unthreaded section 23c of the passage 23. In this section, the pushing member 30 includes a hole 32 configured to receive the instrument shaft 10 therethrough. In greater detail, the hole 32 has a greater width in the direction of the axis T than the width of the instrument shaft 10. At the side which is closer to the second end surface 20b, the hole 32 is defined by a protruding edge 32a that is configured to engage the groove 15 of the instrument shaft 10, thereby forming a locking member for the instrument shaft. Furthermore, on an upper side of the pushing member 30 which is directed towards the top side 21a of the handle portion 20, an elongate recess 33 is formed that is configured to receive a tip 41 of a securing member 40 in the form of a securing screw. The securing screw secures the pushing member 30 in the cutout 26. The elongate recess 33 has its long side oriented in the direction of the axis T. The securing screw is configured to be screwed through a threaded bore 35 extending from the top side 21a of the holding member to the elongate recess 33.

Moreover, a pushing recess 34 is provided in the outer surface of the pushing member 30 to be positioned near the first end surface 20a of the handle portion 20. The pushing recess 34 may be shallow and rounded to be easily found and pushed by a user's fingertip.

In addition, the biasing member in the form of, for example, two biasing springs 50, is placed between the pushing member 30 and the handle portion 20. In greater detail, the biasing springs 50 are arranged in the gap between the first abutment 31a at the pushing member and the first abutment 26a at the handle portion 20 and extend in the lengthwise direction of the handle portion (i.e., in the direction of the axis T). The pushing member 30 can assume a fixing position in which the protruding edge 32a engages the groove 15 of the instrument shaft 10, thereby fixing the instrument shaft to the handle portion. The pushing member can further assume a releasing position in which the protruding edge 32a is disengaged from the groove 15. By means of the biasing member, the pushing member 30 is urged towards the fixing position. The pushing member 30 can be actuated manually into the releasing position by pushing the pushing member inwardly along the axis T. By means of this, the springs 50 are compressed and the protruding edge 32a is moved out of the groove 15. At the same time, the tip 41 of the securing screw moves in a direction parallel to the axis T within and relative to the elongate recess 33. The handle portion 20 can be brought from the fixing position into the releasing position and vice versa by pressing and releasing the pushing member 30. Generally, in the releasing position, the instrument shaft 10 can be inserted or removed.

Furthermore, in the top surface 21a, two attachment recesses 27 may be formed that serve for attachment with a secondary instrument. The attachment recesses 27 are symmetrically arranged on both sides of the center of the handle portion 20 in the lengthwise direction. More specifically, the recesses 27 extend basically on the circumference of a circle around the center of the handle portion, and have a cross-section or shape that includes an undercut 27a at, for example, respective outer sidewalls thereof, which is configured to receive and hold an attachment portion of a secondary instrument therein. It shall be mentioned that the attachment recesses may have other shapes that permit attachment of a portion of the secondary instrument thereto.

The material of the holding portion 20, including its various parts like the pushing member 30, the guiding sleeve 25, and the securing screw 40, may be the same as the material of the instrument shaft 10. However, the handle portion and the respective parts thereof can also be made of one or more other materials. For example, the handle portion can be made of a material that is radiolucent for use in fluoroscopic procedures.

Figure 9:
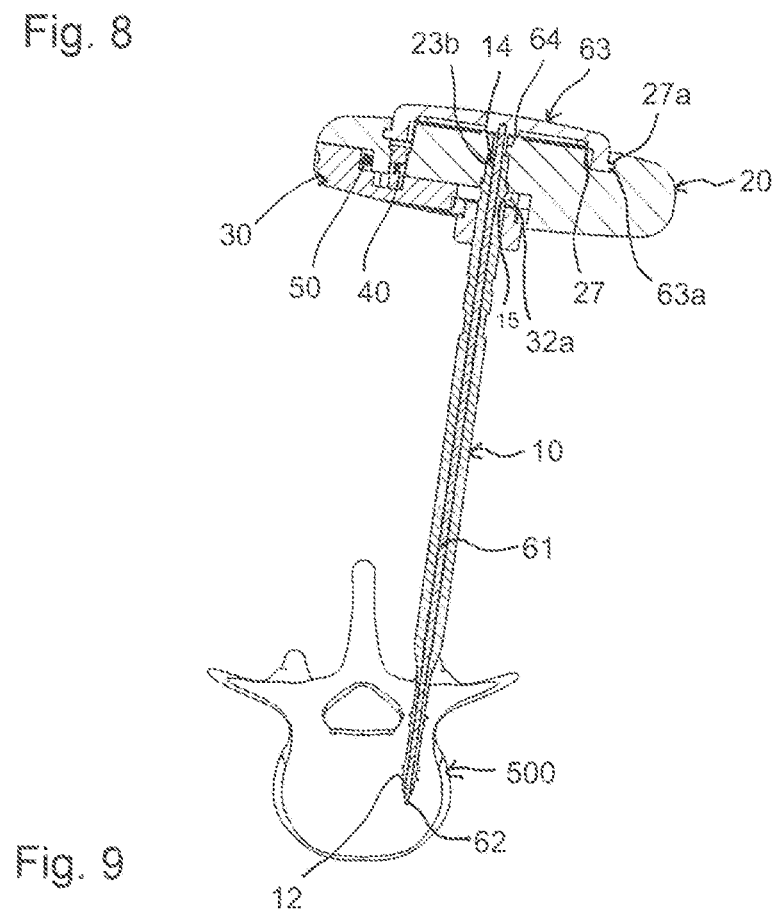
FIG. 9 shows a cross-sectional view of the surgical instrument according to the embodiment of FIGS. 1 to 8, after preparation of a threaded hole in a pedicle of the vertebra.

Next, an example of a secondary instrument 60 in the form of an awl will be explained, with reference to FIGS. 5 to 9. The secondary instrument includes an elongate shaft 61 with a tip portion 62. The elongate shaft 61 is preferably monolithic. The elongate shaft 61 is configured to be inserted into the channel 11 of the instrument shaft 10 and may be adapted to the inner contour of the channel so that, for example, a step 61a may be formed between a main part of the elongate shaft and a front portion which has the tip portion 62. The step 61a is configured to abut against the step 11a in the channel 11 to limit the insertion depth of the elongate shaft 61 into the channel 11. The length of the elongate shaft 61 is such that, in the inserted state, the tip portion 62 projects out of the channel 11. At its rear end opposite to the tip portion 62, the elongate shaft 61 is held in an attachment portion in the form of a bracket 63 extending substantially transversely to the shaft axis of the elongate shaft 61. The bracket 63 includes, at a side facing the handle portion 20 in the assembled state, a sleeve-shaped protrusion 64 that is configured to receive the rear end of the elongate shaft 61, for example, in a press fit manner. An outer diameter of the sleeve-like portion 64 is such that the sleeve-like portion 64 fits into the first portion 23a of the passage 23 of the handle portion 20 (FIG. 9). End portions 63a of the bracket 63 are outwardly protruding and substantially match the shape of a portion of the attachment recesses 27 of the handle portion 20. Hence, when the instrument shaft 10 is assembled with the handle portion 20 and the elongate shaft 61 of the secondary instrument 60 is inserted into the channel 11 of the instrument shaft 10, the length of the bracket 63 and the shape of the end portions is such that the end portions 63a of the bracket 63 matingly engage the attachment recesses 27.

In the assembled state, the attachment portion in the form of the bracket 63 protrudes out of the top surface 21a of the handle portion 20, so that it can be easily gripped and removed when desired. In greater detail, the bracket 63 is configured to assume a fixing position in which the outwardly protruding end portions 63a engage the attachment recesses 27 and are prevented by the undercut 27a from being removed in an axial direction along the shaft axis of the elongate shaft 61. Further, the bracket 63 is configured to assume a releasing position in which the outwardly protruding end portions 63a are disengaged from the attachment recesses 27. The bracket 63 can be moved from the fixing position to the releasing position by rotating the bracket 63.

The material of the elongate shaft 61 with the tip portion 62 is preferably bio-compatible, and can be selected from one of the materials described for the instrument shaft above. The bracket 63 may be made of the same as or of a different material from the shaft 61.

In FIGS. 10a to 10e, steps of assembling the surgical instrument 1 are depicted. The handle portion 20 is shown in a pre-assembled state, with the pushing member 30 and the guiding sleeve 25 mounted. In a first step, as shown in FIGS. 10a and 10b, the instrument shaft 10 is inserted into the guiding sleeve 25 and the pushing member 30 is pushed so that it assumes the releasing position. In this position, the connection portion 14 of the instrument shaft can be advanced into the second portion 23b of the passage until it abuts against the step. Then, the pushing member 30 can be released so that the protruding edge 32a snaps or otherwise protrudes into the groove 15 of the instrument shaft 10. Thereby, the instrument shaft 10 and the handle portion 20 are fixedly connected.

Next, as shown in FIGS. 10c and 10d, the elongate shaft 61 of the secondary instrument is inserted into the channel 11 of the instrument shaft through the top side 21a of the handle portion 20, with the bracket 63 oriented transverse or otherwise angled relative to the longitudinal axis T of the handle portion 20. The insertion depth is defined by the step portion of the elongate shaft 61 abutting against the step portion or shoulder 11a within the channel 11 of the instrument shaft, so that the tip portion 62 extends to a predefined length out of the channel 11. Then, the bracket 63 is rotated so that it engages the attachment recesses 27. Finally, as shown in FIG. 10e, when the outwardly protruding end portions 63a of the bracket have engaged the attachment recesses 27 and more particularly extend into the undercut 27a, the secondary instrument 60 is fixed to the handle portion 20. In this configuration, the secondary instrument 60 is prevented from being removed axially out of the channel of the instrument shaft, and is also secured against rotational forces.

Figure 11E:
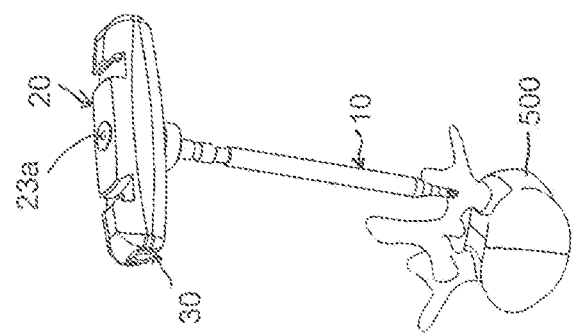
FIGS. 11a to 11e show steps of preparing a threaded hole in the pedicle of a vertebra using the surgical instrument according to the embodiment of FIGS. 1 to 10, with FIG. 11c showing an enlarged portion of FIG. 11b.
Figure 11D:
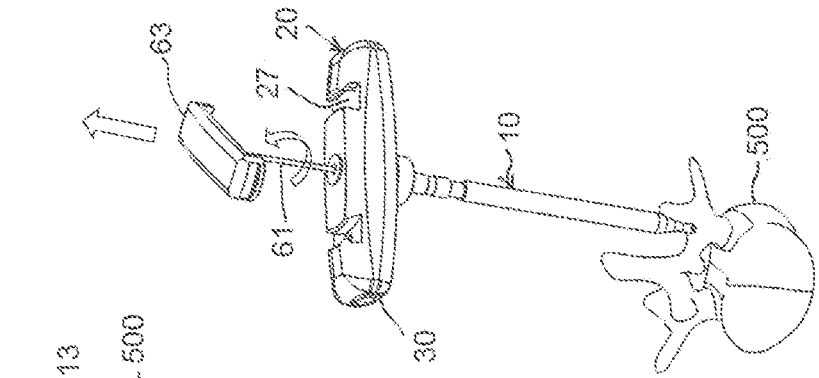
Figure 11C:
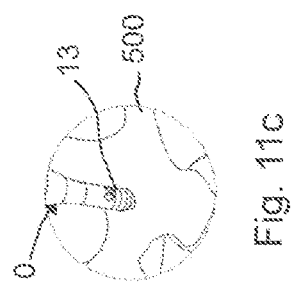
Figure 11B:
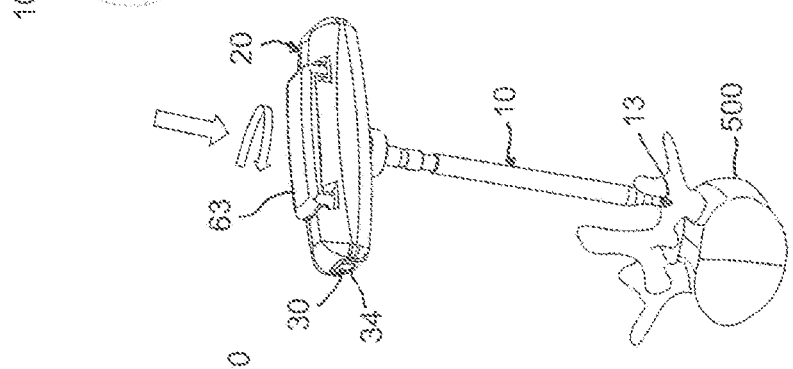
Figure 11A:
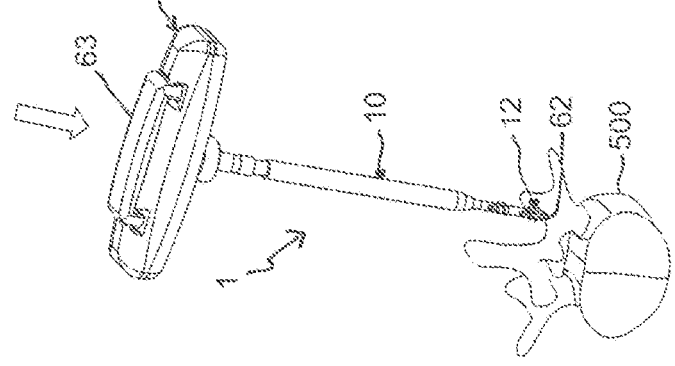

Referring now to FIGS. 11a to 11e, steps of using the functional section 12 of the instrument shaft 10 will be described. Since in the embodiment, the functional section 12 is a thread cutter, a method of cutting a thread into bone is shown. As shown in FIG. 11a, the surgical instrument 1 with the assembled secondary instrument is advanced to an intended site, for example, to the pedicle of a vertebra 500. It shall be understood that prior to using the instrument, at least a small incision in the skin of the patient has been made. As illustrated in FIG. 11b, a hole is made with the tip portion 62 of the awl, and simultaneously the instrument shaft is rotated so that the thread cutting section cuts a thread in the pedicle. With the aid of the depth indication marks 13, the depth achieved can be indicated as shown in FIG. 11c. The whole procedure can be carried out using visualization techniques known in image-based surgery, including navigation and robotics.

Once a required or desired depth has been achieved, or before, the awl can be removed by rotating the bracket 63 and pulling out the elongate shaft 61, as shown in FIG. 11d. The handle portion with the instrument shaft remains in position as depicted in FIG. 11e.

Figure 12C:
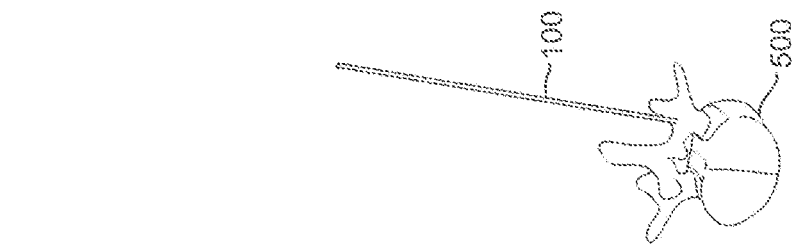
FIGS. 12a to 12c show perspective views of preparatory steps for placing a pedicle screw into the pedicle of a vertebra, where a threaded hole has already been prepared with the surgical instrument according to embodiments of the invention.
Figure 12B:
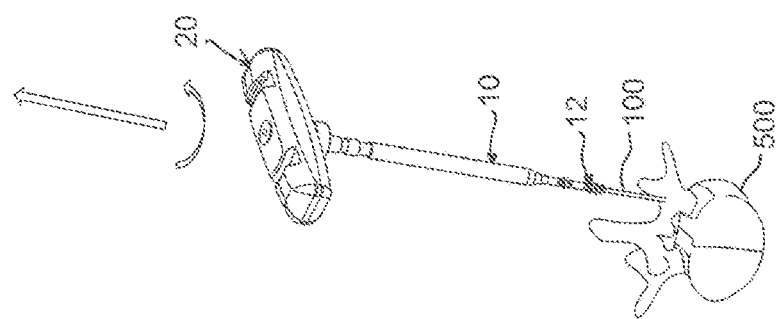
Figure 12A:
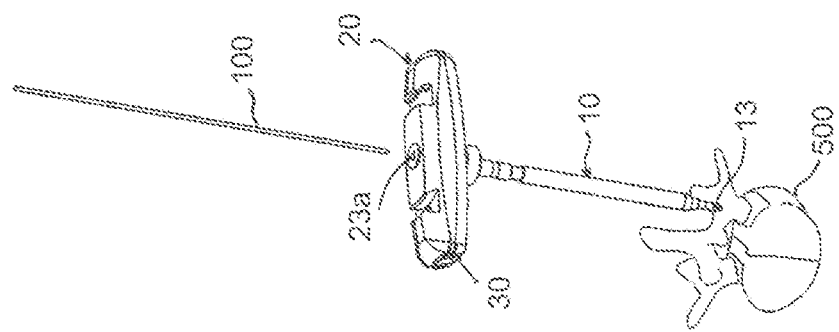

Referring now to FIGS. 12a to 12c, further surgical steps for preparation of the insertion of a pedicle screw are shown. In FIG. 12a, a K-wire 100 is inserted through the first portion 23a of the passage 23 into the channel 11 of the instrument shaft 10 until the K-wire reaches the prepared threaded hole in the pedicle. Once the K-wire has been safely placed, the surgical instrument is removed, for example, as depicted in FIG. 12b by screwing the instrument shaft backward and pulling the surgical instrument away. Now, the K-wire has been placed as shown in FIG. 12c and can be used for guiding a cannulated pedicle screw to the implantation site, and the pedicle screw can be screwed into the prepared hole. Once the pedicle screw has been inserted, the K-wire is removed (not shown).

The described method of placing a bone anchor, such as a bone screw, in a prepared hole is time-saving and more efficient compared, for example, to known techniques, as typical steps requiring Jamshidi needles may become superfluous. Use of the described method also reduces the amount of instrument passes into the body.

Figure 13:
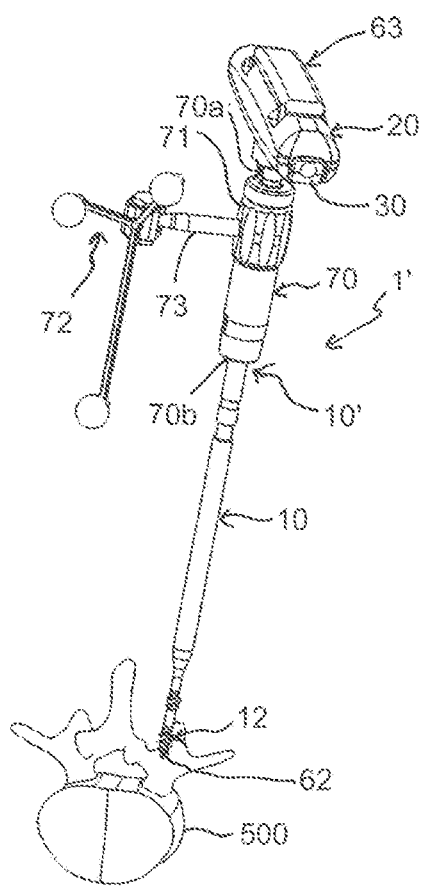
FIG. 13 shows a perspective view of a modified embodiment of the surgical instrument, including an adapter member assembled between the shaft and the handle portion of the surgical instrument.

FIG. 13 shows a modified embodiment that differs from the embodiment according to FIGS. 1 to 12 by the use of an adapter member and a navigation device.

The surgical instrument 1' includes an instrument shaft 10' that includes an instrument shaft 10 similar to the one described in the previous embodiment and an adapter member 70 that may be detachably mounted to the instrument shaft 10. Hence, the instrument shaft 10' is a two part instrument shaft. In greater detail, the adapter member 70 may have a first end 70a with a connection portion configured to be received in the second portion 23b of the handle portion 20 in the same manner as the connection portion 14 described in the previous embodiment. In still greater detail, the first end 70a of the adapter member 70 in the embodiment shown preferably has a quarter inch male connection portion. The second end 70b of the adapter member is configured to be connected to the connection portion 14 of the instrument shaft 10, preferably in a detachable manner. On the adapter member 70, additional auxiliary devices or instruments may be attached. In the embodiment shown, the adapter member 70 includes a rotatable sleeve 71 to which a navigation star 72 is attached via an arm 73. Various other auxiliary devices or instruments can be connected via the adapter member 70 to the instrument shaft 10'. In this embodiment, the length of the secondary instrument, for example, the length of the awl, may be greater than the length of the secondary instrument in the previous embodiment.

Referring to FIGS. 14a to 14d, a further modified embodiment of the surgical instrument 1" will be described. The instrument shaft 10" includes a shank inserting device 80 having a cannulated sleeve with a first end detachably connected to the handle portion 20 and an opposite second end 10b. A head (not shown) of a bone anchor 90, more specifically a head of a bone screw, is firmly held at the second end 10b, so that the threaded shank 91 of the bone screw is axially and rotatably fixed to the shank inserting device 80. The bone screw is cannulated so that the secondary instrument in the form of the awl can be guided therethrough. As depicted in FIG. 14a, when the tip 62 of the awl protrudes out of the shank 91 of the bone anchor, the tip 62 can be used for penetrating the cortical bone. Subsequently, the shank 91 can be screwed into the bone to some extent as shown in FIG. 14b. Next, as illustrated in FIG. 14c, the awl 60 is removed. After removal of the awl 60, the shank can be completely screwed into the bone as illustrated in FIG. 14d. By the method described, use of other instruments like a thread cutter can be omitted.

Figure 15:
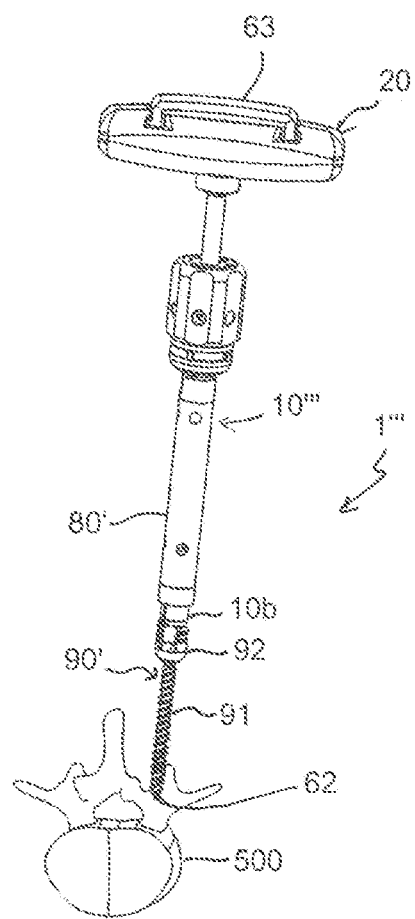
FIG. 15 shows a perspective view of a still further modified embodiment of the surgical instrument.

Referring to FIG. 15, a still further embodiment is shown. The surgical instrument 1''' differs from the embodiment described in FIGS. 14a to 14d in that the instrument shaft 10''' includes a modified shank inserting device 80'. The modified shank inserting device 80' is configured to be releasably connectable with its first end to the handle portion 20 similarly as described in the previous embodiments. At the second end 10b, the modified shank inserting device 80' is connectable to a modified bone anchor 90' that is in the form of a polyaxial bone anchor, where an outer ring 92 is used to clamp and lock a head of an anchoring element in a receiving part. With the modified shank insertion device 80' the threaded shank 91 of the bone anchor 90' is locked and thereby fixedly connected to the handle portion 20. The insertion of the shank 91 into the bone can be carried out in the same manner as described with reference to FIGS. 14a to 14d, i.e., penetrating the cortical bone with the tip portion 62 of the awl 60 and then slightly inserting the shank 91, removing the awl, and then screwing the shank directly into the bone.

The handle portion and at least two instrument shafts with different functional sections form a surgical kit. The different functional sections may encompass different mechanical functions, such as thread cutting, holding and/or fixing, as well as different mechanical variations and/or geometries of one mechanical function. For example, the surgical kit may include the handle portion and two or more instrument shafts with thread cutting portions that differ in terms of diameter and/or other thread characteristics. In addition, the kit may include one or more secondary instruments such as an awl as described and/or a syringe, a K-wire, or a sensor, but not limited to these. It shall be understood that various sub-types of a particular instrument may also be part of the kit such as, for example, awls with a blunt, a sharp, or a threaded tip, or various geometrical modifications thereof. A system may be formed, for example, with the handle portion, one or more instrument shafts, and a cannulated bone anchor.

Various further modifications of the above described embodiments are also conceivable. For example, the detailed shape of the handle portion and the instrument shape are not limited to the shapes shown in the embodiments. Other shapes may also be possible. While the connection between the instrument shaft and the handle portion is shown to be a male and female polygonal connection, other connections may instead be used that allow a releasable connection between the instrument shaft and the handle portion. The mechanism of fixing the instrument shaft to the handle portion may also be different.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A surgical instrument comprising:
   a handle having a first end, a second end, and a passage that extends from the first end to the second end through a portion of the handle having a maximum height measured in a direction of extension of the passage, wherein the maximum height of the handle is less than a length of the handle measured in a direction perpendicular to the direction of extension of the passage;
   a shaft having a first end, a second end, a longitudinal axis extending from the first end to the second end, and a coaxial channel that extends completely through the shaft, wherein the shaft is connectable to the handle when the first end of the shaft is inserted from the second end of the handle into the passage to a position that is closer to the first end of the handle than to the second end of the handle, and wherein the handle comprises an actuator configured to be actuated in a direction parallel to an axis of extension of the length of the handle to release the connection between the handle and the shaft; and
   a secondary instrument comprising an attachment portion that is attachable to the handle in a manner such that a combined maximum height of the handle and the attached secondary instrument remains less than the length of the handle;
   wherein when the shaft and the handle are connected to one another, the secondary instrument is configured to be inserted from the first end of the shaft into the channel and to extend out of the second end of the shaft.

2. The surgical instrument of claim 1, wherein the secondary instrument is insertable from the first end of the handle through the passage of the handle and into the channel of the shaft.

3. The surgical instrument of claim 1, wherein the secondary instrument comprises an elongate shaft with a tip portion.

4. The surgical instrument of claim 1, wherein the secondary instrument comprises an awl.

5. The surgical instrument of claim 1, wherein the handle comprises a first connection surface and the shaft comprises a second connection surface that extends to an end face at the first end of the shaft and that is configured to engage the first connection surface.

6. The surgical instrument of claim 5, wherein the first connection surface and the second connection surface comprise corresponding standardized connection surfaces with axial heights that are less than half of the maximum height of the handle and with respective cross-sections that deviate from respective cross-sections of the handle and the shaft adjacent the first and second connection surfaces.

7. The surgical instrument of claim 5, wherein when the first connection surface and the second connection surface are engaged, the engagement is configured to be locked and released.

8. The surgical instrument of claim 5, further comprising a cannulated adapter comprising a third connection surface structured substantially similarly to the second connection surface for engaging the first connection surface, and a fourth connection surface structured substantially similarly to the first connection surface for engaging the second connection surface, such that the cannulated adapter is configured to be releasably mountable between the shaft and the handle and is configured to connect an auxiliary device to the surgical instrument.

9. The surgical instrument of claim 1, wherein when the actuator is actuated, an overall length of the entire handle remains the same.

10. The surgical instrument of claim 1, wherein the surgical instrument is substantially T-shaped when the handle and the shaft are assembled to one another.

11. The surgical instrument of claim 1, wherein the second end of the shaft comprises a functional section configured to perform a primary function of the surgical instrument.

12. The surgical instrument of claim 11, wherein the functional section comprises a thread cutting portion.

13. The surgical instrument of claim 1, wherein the attachment portion is attachable to the first end of the handle.

14. The surgical instrument of claim 1, wherein the attachment portion comprises a bracket with two ends having respective projections that extend in the direction of extension of the passage to engage attachment recesses on the handle.

15. The surgical instrument of claim 14, wherein the secondary instrument is rotatable to engage the attachment portion with the attachment recesses on the handle.

16. The surgical instrument of claim 1, further comprising a cannulated adapter releasably mountable to other portions of the surgical instrument, with at least a portion of the cannulated adapter positioned axially between part of the shaft and part of the handle, wherein the adapter is configured to connect an auxiliary device to the surgical instrument.

17. A system comprising the surgical instrument of claim 1 and a cannulated bone anchor.

18. The surgical instrument of claim 1, wherein an opening of the passage defined at the first end of the handle is smaller than an opening of the passage defined at the second end of the handle to form a stop therebetween, such that the first end of the shaft is configured to abut against the stop when the shaft is inserted in the handle.

19. A surgical kit comprising:
a handle having a first end, a second end, and a passage that extends from the first end to the second end through a portion of the handle having a maximum height measured in a direction of extension of the passage, wherein the maximum height of the handle is less than a length of the handle measured in a direction perpendicular to the direction of extension of the passage;
a first shaft having a first end, a second end, a longitudinal axis extending from the first end to the second end, and a coaxial channel that extends completely through the shaft;
a second shaft having a first end, a second end, a longitudinal axis extending from the first end to the second end, and a coaxial channel that extends completely through the shaft, wherein the first and second shafts are interchangeably connectable to the handle by inserting the first end of the selected shaft from the second end of the handle into the passage to a position that is closer to the first end of the handle than to the second end of the handle, and wherein the handle comprises an actuator configured to be actuated in a direction parallel to an axis of extension of the length of the handle to release the connection between the handle and the selected shaft; and
a secondary instrument comprising an attachment portion that is attachable to the handle in a manner such that a combined maximum height of the handle and the attached secondary instrument remains less than the length of the handle;
wherein when one of the first or second shafts is connected to the handle, the secondary instrument is configured to be inserted from the first end of the connected shaft into the channel of the connected shaft and to extend out of the second end of the connected shaft.

20. A method of assembling a surgical instrument comprising a handle having a first end, a second end, and a passage that extends from the first end to the second end through a portion of the handle having a maximum height measured in a direction of extension of the passage, wherein the maximum height of the handle is less than a length of the handle measured in a direction perpendicular to the direction of extension of the passage, a shaft having a first end, a second end, a longitudinal axis extending from the first end to the second end, and a coaxial channel that extends completely through the shaft, wherein the shaft is connectable to the handle, and wherein the handle comprises an actuator configured to be actuated in a direction parallel to an axis of extension of the length of the handle to release the connection between the handle and the shaft, and a secondary instrument, the method comprising:
inserting the first end of the shaft from the second end of the handle into the passage to a position that is closer to the first end of the handle than to the second end of the handle to connect the shaft to the handle;
inserting the secondary instrument from the first end of the handle into the passage to the first end of the shaft and from the first end of the shaft into the channel until the secondary instrument extends out of the second end of the shaft; and engaging an attachment portion of the secondary instrument with the handle to hold an axial position of the secondary instrument relative to the handle and the shaft, wherein when the attachment portion of the secondary instrument is engaged with the handle, a combined maximum height of the handle and the attached secondary instrument remains less than the length of the handle.

\* \* \* \* \*